United States Patent
Pfreudschuh et al.

(10) Patent No.: US 9,469,678 B2
(45) Date of Patent: Oct. 18, 2016

(54) NY-ESO-1 PEPTIDES WHICH BIND TO CLASS II MOLECULES AND USES THEREOF

(75) Inventors: Michael Pfreudschuh, Homburg (DE); Frank Neumann, Homburg (DE); Hans-George Rammensee, Tubingen (DE); Stefan Stevanovic, Tubingen (DE)

(73) Assignee: LUDWIG INSTITUTE FOR CANCER RESEARCH, New York, NY (US)

( * ) Notice: Subject to any disclaimer, the term of this patent is extended or adjusted under 35 U.S.C. 154(b) by 2946 days.

(21) Appl. No.: 10/547,896

(22) PCT Filed: Mar. 1, 2004

(86) PCT No.: PCT/US2004/006341
§ 371 (c)(1),
(2), (4) Date: Apr. 11, 2008

(87) PCT Pub. No.: WO2004/078776
PCT Pub. Date: Sep. 16, 2004

(65) Prior Publication Data
US 2008/0187548 A1    Aug. 7, 2008

Related U.S. Application Data

(60) Provisional application No. 60/452,074, filed on Mar. 4, 2003.

(51) Int. Cl.
*A61K 38/00* (2006.01)
*A61K 38/04* (2006.01)
*A61K 38/08* (2006.01)
*A61K 38/10* (2006.01)
*C07K 14/47* (2006.01)
*A61K 38/17* (2006.01)

(52) U.S. Cl.
CPC .......... *C07K 14/4748* (2013.01); *A61K 38/00* (2013.01); *A61K 38/04* (2013.01); *A61K 38/08* (2013.01); *A61K 38/10* (2013.01); *A61K 38/1764* (2013.01)

(58) Field of Classification Search
None
See application file for complete search history.

(56) References Cited

PUBLICATIONS

Zeng et al (J. Immunol. 2000, 165(2): 1153-1159).*
Wang and Rosenberg (Immunol. Rev., 1999 170: 85-100).*
Rammensee et al (Immunogenetics, 1999 50: 213-219).*
Chen et al (PNAS, 1997, 94: 1914-1918.*
Thibodeau (Oncolmmunology 1:6, 908-916; Sep. 2012 Landes Bioscience).*

* cited by examiner

*Primary Examiner* — Gerald R Ewoldt
*Assistant Examiner* — Marianne Dibrino
(74) *Attorney, Agent, or Firm* — Abelman, Frayne & Schwab

(57) ABSTRACT

The invention relates to peptides which consist of amino acid sequences found in the NY-ESO-1 molecule, which bind to MHC-Class II molecules. These can be used alone, or in combination with other peptides.

7 Claims, No Drawings

NY-ESO-1 PEPTIDES WHICH BIND TO CLASS II MOLECULES AND USES THEREOF

RELATED APPLICATIONS

This application is a §371 of International Application No. PCT/US2004/06341 filed Mar. 1, 2004, and claims priority from U.S. Provisional Patent Application No. 60/452,074 filed Mar. 4, 2003, both incorporated by reference in their entireties.

FIELD OF THE INVENTION

This invention relates to HLA binding peptides derived from an antigen associated with cancer. These peptides bind to Class II MHC molecules.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecule which encode a particular marker, followed by the use of the isolated encoding molecule to express the desired molecule.

To date, two strategists have been employed for the detection of such antigens, in e.g., human tumors. These will be referred to as the genetic approach and the biochemical approach. The genetic approach is exemplified by, e.g., dePlaen et al., Proc. Natl. Sci. USA 85:2275 (1988), incorporated by reference. In this approach, several hundred pools of plasmids of a cDNA library obtained from a tumor are transfected into recipient cells, such as COS cells, or into antigen-negative variants of tumor cell lines which are tested for the expression of the specific antigen. The biochemical approach, exemplified by, e.g., O. Mandelboim, et al., Nature 369:69 (1994), incorporated by reference, is based on acidic elution of peptides which have bound to MHC-Class I molecules of tumor cells, followed by reversed-phase high performance liquid chromography (HPLC). Antigenic peptides are identified after they bind to empty MHC-Class I molecules of mutant cell lines, defective in antigen processing, and induce specific reactions with cytotoxic T-lymphocytes. These reactions include induction of CTL proliferation, TNF release, and lysis of target cells, measurable in an MTT assay, or a $^{51}$Cr release assay.

These two approaches to the molecular definition of antigens have the following disadvantages: first, they are enormously cumbersome, time-consuming and expensive; and second, they depend on the establishment of cytotoxic T cell lines (CTLs) with predefined specificity.

The problems inherent to the two known approaches for the identification and molecular definition of antigens is best demonstrated by the fact that both methods have, so far, succeeded in defining only very few new antigens in human tumors. See, e.g., van der Bruggen, et al., Science 254:1643-1647 (1991); Brichard, et al., J. Exp. Med. 178:489-495 (1993); Coulie, et al., J. Exp. Med. 180:35-42 (1994); Kawakami, et al., Proc. Natl. Acad. Sci. USA 91:3515-3519 (1994).

Further, the methodologies described rely on the availability of established, permanent cell lines of the cancer type under construction. It is very difficult to establish cell lines from certain cancer types, as is shown by, e.g., Oettgen, et al., Immunol. Allerg. Clin. North. Am. 10:607-637 (1990). It is also known that some epithelial cell type cancers are poorly susceptible to CTLs in vitro, precluding routine analysis. These problems have stimulated the art to develop additional methodologies for identifying cancer associated antigens.

One key methodology is described by Sahin, et al., Proc. Natl. Acad. Sci. USA 92:11810-11913 (1995), incorporated by reference. Also, see U.S. Pat. No. 5,698,396, incorporated by reference. To summarize, the method involves the expression of cDNA libraries in a prokaryotic host. (The libraries are secured from a tumor sample). The expressed libraries are then immunoscreened with absorbed and diluted sera, in order to detect those antigens which elicit high titer humoral response. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin, et al., supra, as well as Crew, et al., EMBO J. 144:2333-2340 (1995).

One important antigen identified by the SEREX methodology is referred to as NY-ESO-1. The antigen is described in, e.g., U.S. Pat. No. 5,804,381, and Chen, et al., Proc. Natl. Acad. Sci. USA 94:1914-1918 (1997), the disclosures of which are incorporated by reference. Originally, NY-ESO-1 was characterized as an antigen which was processed into peptides presented by MHC Class I molecules. Later work showed that it also processed into peptides that are presented by Class II molecules. See Jäger, et al., J. Exp. Med. 191:625 (2000), as well as PCT application publication number WO99/53938, published Oct. 28, 1999, both of which are incorporated by reference in their entirety. Also, see WO 01/23560, also incorporated by reference. Additional papers have been published which describe additional peptides which consist of amino acid sequences found in NY-ESO-1, which also bind to MHC Class II molecules and serve as T cell epitopes. Exemplary are Zeng, et al., J. Immunol. 165:1153-1159 (2000); Zarour, et al., Canc. Res. 60:4946-4952 (2000); Zarour, et al., Canc. Res. 62:213-218 (2002); Zeng, et al., Proc. Natl. Acad. Sci. USA 98(7):3964-3969 (2001), and Zeng, et al., Canc. Res. 62:3630-3635 (2002), all of which are incorporated by reference.

The interest in such molecules results from several factors. First, NY-ESO-1 appears to be restricted in its expression to tumor cells, of various histological types, and male germ cell lines. Exemplary of the tumor types in which NY-ESO-1 expression is found are melanoma, breast, prostate, lung, urinary bladder, carcinoma, and synovial sarcoma. See Jäger, et al., supra. Also see Chen, et al., supra, Stockert, et al., J. Exp. Med. 187:1349 (1998); Wang, et al J. Immunol. 161:3598-3606 (1998); Jungbluth, et al. Int. J. Cancer 92:856-860 (2001); Jungbluth, et al, *Int. J. Cancer* 94:252-256 (2001); all incorporated by reference.

The fact that T cells play an important role in controlling tumor growth and mediating tumor regression is well known. The molecular mechanisms underlying T cell mediated anti-tumor immunity has been elucidated, inter alia by the identification of tumor antigens that are recognized by $CD8^+$ T cells. See Rosenberg, Immunity 10:281-287 (1998); Wang, et al., Immunol. Rev. 170:85-100 (1999). The advances in the identification of such molecules have led to their use in clinical trials, examples of which may be seen in Rosenberg, Nature 411:380-384 (2001). Also see Nestle, et al., Nat. Med. 4:328-332 (1998); Rosenberg, et al., Nat. Med. 4:321-327 (1998); Lee, et al., J. Clin. Oncol. 19:3836-3847 (2001); Thurner, et al., J. Exp. Med. 190:1669-1678 (1999).

The growing interest in Class II presentation stems, in part, from animal model studies that indicate that it may be necessary to engage $CD4^+$ cells as well as $CD8^+$ cells in order to develop effective cancer vaccines. See Zeng, J. Immunother 24:195-204 (2001).

To move from the general back to the specific, NY-ESO-1, as has been pointed out, supra, shows strict tumor expression. In addition to the $CD8^+$ response noted supra, high titers of NY-ESO-1 antibodies were present in patients who express the molecule, suggesting that there is a $CD4^+$ response involved. See Wang, et al, Immunol. Rev. 179:85-100 (1999); Pardoll, et al., Curr. Opin. Immunol 10:588-594 (1998); and Jager et al., Proc. Natl. Acad. Sci. USA 97:4760-4765 (2000). While NY-ESO-1 derived peptides ("derived" as used herein, refers to amino acid sequences which can be found in the NY-ESO-1 protein sequence described in the Chen '381 patent and PNAS paper cited supra) have been identified which are presented by HLA-DRB1*0401 and HLA-DRB1*0101 (Zeng, et al., J. Immunol. 165:1153-1159 (2000), Jäger, et al., J. Exp. Med. 191:625-630 (2000)), the majority of patients who present NY-ESO-1 specific antibodies do not present these MHC-Class II molecules. Hence, there is an interest in finding additional peptides, derived from NY-ESO-1, which bind to MHC-Class II molecules, for all of the reasons described supra. Further, there is a need to extend the use of peptide vaccines to patients who do not present MHC-Class II molecules.

There are various "rules" or "guidelines" for determining if a peptide of interest should bind to a given MHC or HLA molecule. See, for example, Marsh, et al., *The HLA Factsbook* (Academic Press, 2000), which presents a listing of "binding motifs" for determining the likelihood of a peptide binding to a particular MHC Class I or Class II molecule. There are also numerous algorithms and programs available to facilitate this review. See, e.g., Southwood, et al., J. Immunol. 160:3363 (1998); Honeyman, et al., Nat. Biotechnol. 16:966-969 (1998); Breisie, et al., Bioinformatics 14:121-131 (1998), as well as the "SYFPEITHI" algorithm, referred to infra. As will be shown, experimental conformation of these algorithms is always required before any conclusions can be drawn. The common occurrence of false positives is a major drawback of algorithm defined, HLA binding peptides.

The disclosure which follows identifies a new, promiscuous Class II binding peptide, derived from NY-ESO-1. The ramifications of this discovery are also a part of this invention, as will be seen from the disclosure which follows.

DETAILED DESCRIPTION OF PREFERRED EMBODIMENTS

EXAMPLE 1

The NY-ESO-1 molecule was screened, using the publicly available SYFPEITHI algorithm, which is available at www.syfpeithi.de and is incorporated by reference. The amino acid sequence of NY-ESO-1 which was used is found at U.S. Pat. No. 5,804,381, and Chen, et al., Proc. Natl. Acad. Sci. USA 94:1914-1918 (1997), both of which are incorporated. Binding motifs for three HLA-DRB1 subtypes were used, i.e., those for subtypes *0101, *0301, and *0401, which make up 27% of the Caucasian population. Further, the motif for subtype *0701 was also used, because it is found in an additional 12% of the Caucasian population, and shares most of its anchor positions with *0401.

Via application of the algorithm, three peptides were identified, corresponding to amino acid 91-105 (YLAMPFATPMEAELA; SEQ ID NO: 1); 134-148 (TIRLTAADHRQLQLS; SEQ ID NO: 2), and 158-172 (LLMWITQCFLPVFLA, SEQ ID NO: 3). These peptides, based upon the published motifs in the algorithm cited supra, should show a maximum range of promiscuous binding to the selected HLA-DRB1 molecules. The peptides were synthesized, via the known, Fmoc/tBu strategy of Lang, et al, Cell Mol. Life. Sci. 59:1076-1080 (2002), which was also followed for the syntheses of a mix of peptides derived from p65 of Human CMV (p32, p117, p243, p269, p299, p510 and p524), which were used as positive controls, based upon the algorithm.

The purity of the peptides was greater than 90% as determined by HPLC and mass spectrometry. The peptides were dissolved completely in water and DMSO. The peptides were brought to a concentration of 2 ug/ml for pulsing experiments, described infra, with DSMO concentration during APC pulsing remaining at less than 1%, v/v.

EXAMPLE 2

Following the preparation of the peptides, peripheral blood mononuclear cells ("PBMCs", hereafter) were obtained from cancer patients for testing.

PBMCs were isolated from patients using commercially available Ficoll-separation methods. Following isolation, samples of unseparated PBMCs ($1 \times 10^7$ cells in toto for each patient), were divided into at least three vials and frozen until used in assays, described infra. Remaining cells were divided into aliquots of $4 \times 10^6$ cells. Each aliquot was pulsed with a different peptide, at a concentration of 2 ug peptide/ ml, by incubating the cells and the peptides for 2 hours, at 37° C., in a volume of 500 ul serum free medium (RPMI 1640, 2 mM L-glutamine, 1% penicillin/streptomycin).

Following pulsing, cells were washed, once, with serum free medium, and were then suspended for cultivation in commercially available medium, at a density of $4 \times 10^6$ cells/2 ml, to which was added 5 ng/ml IL-7 and 10% human AB serum and IL-20 u/ml on day 1. The samples were then divided into two wells.

Whether the PBMCs were to be used as antigen presenting cells ("APCs"), or as a source of effector cells, these were incubated for 6 days, and examined occasionally microscopically. If cells proliferated strongly, the samples were split. A total of 29 patient samples were stimulated with SEQ ID NO: 1, 38 with SEQ ID NO: 2, and 21 with SEQ ID NO: 3. The samples were taken from a pool of 41 patients, 35 of whom had lung cancer, 2 had pleural mesothelioma, and 4 had breast cancer. Most of the lung cancer patients had measurable disease, and were undergoing some form of chemotherapy and/or radiotherapy at the time of these experiments. Only one lung cancer patient and the four breast cancer patients were the only ones who had been operated upon.

In this first ELISPOT assay, $5 \times 10^4$ autologous PBMCs which had been pulsed with peptide, as described supra, were used as the antigen presenting cells. Either $2.5 \times 10^4$, or $1.25 \times 10^4$ sensitized CD4+ T cells were added per well, to serve as effectors. The sensitized CD4+ cells were harvested from the wells described supra. Any remaining cells were re-stimulated with autologous PBMC which had been pulsed with one of the peptides, as described supra at a CD4+/APC ratio of 1:1. A second ELISPOT assay was carried out on day 14, and a final one, on day 21.

The ELISPOT assays followed standard protocols for such assays. In brief, the PBMCs which served as APCs were irradiated with 30 Gy. These APCs and effector cells (each of which were suspended at 50 ul/well) were co-incubated, for 14-16 hours at 37° C., in wells that had been precoated the day before, for 16 hours at 4° C., with anti-IFN-γ capture antibody. In addition to the instructions which came with ELISPOT kit, a blocking step was carried out, using 10% (v/v) human AB serum, for 1 hour at 37° C. after the wells had been coated. The sensitivity of IFN-γ detection was enhanced by incubation for 1 hour with alkaline phosphatase conjugated streptavidin, which had been diluted 1:500 in PBS, which was added after incubation with biotinylated, anti-IFN-γ antibody and removal (by washing), of unbound biotinylated antibody. A commercially available kit was used to stain IFN-γ spots, and assays were preformed, in triplicate, in nitrocellulose lined 96 well plates.

In addition to the assays described supra, controls were run. In a first set of controls, $1.5 \times 10^5$ SK-MEL 37 cells were used as APCs, and were suspended in 190 ul of fresh medium, together with 10 ul of commercially available anti-pan human MHC-II antibody, and incubated for 30 minutes at 37° C. The cells were washed, gently spun, and resuspended in the same medium as the PBMCs, and were dispensed into three wells.

No reproducible T cell responses were obtained after stimulation with either SEQ ID NO: 1 or 3, notwithstanding the predictions based on the algorithm. In contrast, SEQ ID NO: 2 was strongly immunostimulatory. Of the 38 patients tested, seven (18%) showed a response upon stimulation with the peptide. Of the seven positives, three patients developed a moderate, but clearly positive reaction after day 14 (the second stimulation), while four developed a strong response after the first stimulation.

EXAMPLE 3

The experiments described in this example were designed to prove the HLA molecule presenting the peptide of SEQ ID NO: 2 is restricted to specific CTL stimulation. The PBMCs used as the APCs in the ELISPOT assay of example 2, supra, were treated similarly to the SK-MEL 37 cells used as a control. Specifically, $1.5 \times 10^5$ PBMCs were suspended in 50 ul of fresh medium, together with 20 ul of commercially available anti HLA-DR antibody, and incubated for 30 minutes at 37° C. An additional control was used, where 20 ul of a commercially available anti-HLA-DP antibody was added to the cells. The sample volume was increased to 500 ul with buffer, and then peptide was added, at 2 ug/ml. The cells were incubated for another 30 minutes at 37° C., and were then washed, spun down, and re-suspended in buffer. The cells were then dispensed into three wells, and subjected to an ELISPOT assay, as described supra.

The results indicated that the anti-HLA-DR antibody blocked all activity with SEQ ID NO: 2, whereas anti-HLA-DP had no effect, confirming that SEQ ID NO: 2 is presented by an HLA-DR molecule.

EXAMPLE 4

The experiments reported in the prior example showed that the peptide defined by SEQ ID NO: 2 was presented by an HLA-DR molecule. The experiments described herein were designed to delineate the HLA-DR restriction of the peptide, and the subtype of patients responding to the peptide, as well as those who did not.

Standard HLA-SSP PCR was carried out on the samples, using standard methods. The results are presented in Table 1 which follows:

|  | HLA-DRB1 . . . | | | |
| --- | --- | --- | --- | --- |
|  | *0101 | *0301 | *0401 | *0701 |
| Allele frequency (n = 76) | 7 | 10 | 7 | 7 |
| Responding patients (n = 38) | 2 | 1 | 2 | 1 |
| Responding patients (%) | 28.6% | 10% | 28.6% | 14.3% |
| SYFPEITHI-Score | 25 | 19 | 26 | 22 |

It will be seen from Table 1 that the binding of SEQ ID NO: 2 was restricted to HLA-DRB1*0101, *0301, *0401, and *0701 subtypes, and is the first demonstration of promiscuous peptide binding T cell recognition.

Five non-responding patients were also HLA-DR typed. Three of them had no subtype with a high binding score for SEQ ID NO: 2. Two were typed as HLA-DBR*0701/*1501 and *0301/*1501.

EXAMPLE 5

Following the experiments described supra, the data were analyzed to determine if the HLA-DRB1 subtype distribution of the 38 patients was representative of the normal population. To do this, the distribution HLA-DRB1 subtypes of the 11 patients who were analyzed by SSP-PCR was compared to a reference population, as described by Albert, "Immunogenetik" in Gemsa, et al, ed., *Immunologie* (1997). The patient profile matched the population at a very high level (p=0.9431 for exact evaluation, p=0.9955 for asymptolicol evaluation via Chi squared test), implying that the frequency of positive T cell response observed during peptide stimulation was due to restricted peptide binding, and not to disproportionate occurrence of responder subtype.

EXAMPLE 6

As was noted, supra, all patients who exhibited the subtypes of HLA-DRB1 to which SEQ ID NO: 2 was predicted to bind (with the exception of DRB1*0701), the data obtained via blocking with the anti HLA-DR antibody and the failure of the anti HLA-DP antibody to block demonstrated HLA-DR restriction. As further confirmation, a functional peptide displacement titration was carried out.

To do this, T cells were stimulated with SEQ ID NO: 2, as described supra. In addition, APCs to be used in an ELISPOT assay were pulsed, with SEQ ID NO: 2, in the presence of increasing concentrations of PADRE, which is an acronym for "pan-DR-binding T-helper epitope. See U.S.

Pat. No. 5,736,142, and Alexander, et al., Immunity 1(9): 751-761 (1994). To elaborate, PBMCs were pulsed with SEQ ID NO: 2 at a concentration of 2 ug/ml, 2 ug/ml plus 1 ug/ml of PADRE, 2 ug/ml of both peptides, or 2 ug/ml of PADRE only. The cells were then subjected to an ELISPOT assay, as described supra As the amount of PADRE increased, the number of spots generated by IFN-γ secreting CD4+ cells decreased, resulting from displacement of SEQ ID NO: 2 by PADRE with which it competes, providing confirmation of binding of SEQ ID NO: 2 to this HLA-DR.

EXAMPLE 7

The experiments set forth in this example were designed to determine if SEQ ID NO: 2 was naturally processed and presented following endogenous expression of NY-ESO-1.

To do this, two melanoma tumor lines were selected, which had been shown, previously, to express NY-ESO-1, and at similar levels. These cell lines, i.e., SK-MEL-37 and Me275, express different HLA-DR molecules. SK-MEL-37 expresses HLA-DRB1*0101/*0301, while Me275 is homologous for HLA-DRB1*1302.

T cells were taken from a DRB1*0301 positive patient, and were prestimulated with SEQ ID NO: 2.

The T cells were then tested against the cancer cell lines in an ELISPOT assay of the type described supra the only change being that the cell lines were irradiated with 120 Gy. The T cells recognized and were stimulated by SK-MEL-37 to produce IFN-γ, but not Me275, confirming natural processing and presentation of SEQ ID NO: 2 by SK-MEL-37 and corresponding recognition of SEQ ID NO: 2 peptide when presented to T cells.

In follow up experiments, the cell lines were pulsed, twice, resulting in doubling of the IFN-γ spots, as compared to untreated SK-MEL-37 cells Me275 remained unrecognized, providing further evidence that SEQ ID NO: 2 binds to DRB1*0101/*0301 molecules, but not the DRB1*1302 molecules on Me275 cells.

EXAMPLE 8

Further work was carried out to determine whether there was a difference in rate of reactivity of SEQ ID NO: 2 among patients with different subtypes. The rate of response or responding patients with given subtypes of HLA-DR was analyzed, and is summarized in Table 1, supra. The rate of response of patients with one of the four responding subtypes corresponded to that predicted by the SYFPEITHI algorithm, referred to supra There was a linear correlation between both parameters ($R^2=0.92$, $p=0.04$), demonstrating the validity of the algorithm and confirming that SEQ ID NO: 2 bound and recognized HLA-DR in a restricted matter.

EXAMPLE 9

These experiments describe flow cytometry based work for characterizing effector cells, APCs, and cell lines.

In order to analyze the cells, approximately $1 \times 10^5$ cells of each type were harvested at day 0, and one day before each ELISPOT assay. The cells were washed, spun down gently, and the resulting pellet was resuspended in 90 ul of staining buffer, A 5 ul sample of three antibodies, i.e., anti-HLA-DR-PE, anti-hCD4/FITC, or anti-hCD8/PE were added, mixed, and incubated at 4° C., for 20 minutes. Following a washing step, cells were resuspended in a washing solution, and $5 \times 10^4$ cells were analyzed, using a commercially available FACS scanner.

Among the observations from these experiments was the confirmation that SK-MEL-37, known to express HLA-DRB1*0101 and *0301, as expressed in Example 7, showed strong expression of DR molecules by PADRE analysis. When experiments were repeated, at different temperatures and after irradiation with 120 Gy, no influence on DR expression was seen.

Further work was also done using tumor biopsies to demonstrate the expression of HLA-DR histologically. In brief, sections were taken from tumor biopsies, fixed with formalin immediately, embedded in paraffin, and mounted. Following mounting sections were treated to remove the paraffin, and were rehydrated, exposed to hydrogen peroxide (3%, v/v), and subjected to antigen retrieval via incubation in 110 mM citrate buffer (pH 6.0), and heating in a microwave oven at 750 VA followed by 350 VA, for 5 minutes. The slides were blocked with PBS/1% BSA (v/v), and 20% rabbit serum for 20 minutes at room temperature and incubated for 30 minutes at 37° C., with monoclonal murine anti-human HLA-DR/a chain diluted 1:50 in PBS/1% rabbit serum (v/v). Slides were then washed, twice, in PBS, and sections were incubated for 15 minutes at 37° C. in biotinylated rabbit-anti mouse immunoglobulin, diluted 1:300 in PBS. Following a final PBS wash, DAB substrate was added, and slides were counterstained with hematoxylin. As a negative control, and irrelevant, isotype matched primary antibody was used. The histochemical staining also revealed that the HLA-DR molecules were expressed strongly in tumor biopsies.

With respect to the flow cytometry assay, the results indicated that the T cell response to SEQ ID NO: 2 induced IFN-γ production, and also resulted in proliferation and expansion of the responding T cells. The expansion was due to CD4+ cells, for the most part, as was demonstrated by their increase within the lymphocyte gate following stimulation with the peptide. This was especially true in patients who had a strong peptide induced T cell response.

EXAMPLE 10

These experiments describe correlation between T cell and humoral anti-NY-ESO-1 responses. As was noted, supra, 38 patients were tested for a T cell response to SEQ ID NO: 2. Samples from these patients were also tested for serum antibodies against NY-ESO-1, via Western blot and ELISA, using NY-ESO-1 protein expressed in E. coli. See Stockert, et al, J. Exp. Med. 187:1349-1354 (1998), incorporated by reference, for these methodologies, as well as U.S. Pat. No. 6,252,052, also incorporated by reference. Only 5 patients had NY-ESO-1 antibodies in their serum. Of the 38 patients, 3 were antibody positive but no T cell response could be induced. Two of four patients with strong T cell response were also positive for antibodies, and three patients with a moderate T cell response were antibody negative. No association could be drawn between responders and high responders for a given HLA-DRB1 phenotype.

The foregoing examples describe the isolation and characterization of a peptide derived from NY-ESO-1, which binds, ubiquitously, to MHC Class II molecules, and acts as a T cell epitope for CD4+ cells when bound to such molecules. The peptide may be used alone, or in combination with one or more other peptides that are presented by Class II molecules, as well as in combination with one or more peptides presented by MHC-Class 1 molecules. Such peptide "cocktails," comprising SEQ ID NO: 2 and at least one other peptide presented by an MHC molecule, be it a Class I or a Class II molecule, are a further feature of the invention.

The peptide of SEQ ID NO: 2, as well as the cocktails described herein, may be combined with an adjuvant, or may be used as they are. Such cocktails may include other NY-ESO-1 derived peptides, peptides derived from other tumor rejection antigen precursors, such as, but not being limited to members of the MAGE family, SSX2, SCP1, as well as mixtures thereof.

For example, there is a known homologue of NY-ESO-1, known as LAGE. Homologues of the peptides referred to supra are FIRLTAADHRQLQLS (SEQ ID NO: 4) and HITMPFSSPMEAELV (SEQ ID NO: 5). These LAGE peptides, both alone and in combination with other peptides, are a further feature of the invention. These peptides are representative of LAGE peptides which bind to MHC-Class II molecules, which can be used alone or in combination with the other peptides described herein.

A further feature of the invention relates to extensions of the amino acid sequence of SEQ ID NO: 2, to produce peptide molecules which contain both SEQ ID NO: 2 as well as an amino acid sequence corresponding to a peptide which binds to at least one other MHC molecule, be it Class I or Class II. Gnjactic, et al, J. Immunol. 170:1191-1196 (2003); Zeng, et al., Canc. Res. 62:3630-3635 (2002), incorporated by reference, teaches that a single peptide may be processed intracellularly to from both Class I and Class II binders. The invention relate to such extended structures, both in isolated form, and in "cocktail" form, as is described supra.

Peptides such as those described herein are useful clinically, in view of the observations, set forth herein and elsewhere, that both antibodies and CTLs against NY-ESO-1 have been detected in patients with cancer. Via the use of the peptides and cocktails of the invention, one may induce NY-ESO-1 specific $CD4^+$ & $CD8^+$ T cells, as well as antibodies specific for the molecule. In parallel fashion, antigen presenting cells, such as, but not being limited to, dendritic cells, loaded with the peptide or peptides, or infected with vectors expressing such peptides, may be used as therapeutic agents. As was pointed out, supra, NY-ESO-1 expression is limited to cancer cells and testicular germ cells; however, the latter do not express MHC molecules, and thus are not subject to T cell attack by $CD4^+$ or $CD8^+$ cells of the type described herein. See, e.g., Marchand, et al., Int. J. Cancer 80:219 (1999); Thurner, et al., J. Exp. Med. 190:1669 (1999), validating this principle in parallel systems.

As noted, supra, the peptides of the invention leads to generation of therapeutically useful, $CD4^+$ cells. Such cells can be separated from cell populations, using standard techniques. The resulting, isolated $CD4^+$ cells are a feature of the invention, as is their use in therapy, either alone or in combination with another therapeutic agent, such as $CD8^+$ cells. So, too, can one of ordinary skill in the art generate soluble TCRs from the $CD4^+$ and/or $CD8^+$ cells, and utilize these in assay, such as assays designed to monitor forms of therapy, and/or detection of cancer, as well as its progression, regression, or stasis. See WO 99/60120, WO 02/086740 and WO 99/60120, all of which are incorporated by reference.

Also a part of the invention are isolated nucleic acid molecules which consist of nucleotide sequences that encode the peptide of, e.g., SEQ ID NO: 2 including expression vectors. One such sequence can be seen in U.S. Pat. No. 5,804,381, and given the degeneracy of the genetic code, other sequences can be developed as well. These nucleic acid molecules can be used, e.g., in expression vectors, which in turn can be used to transform or transfect cells, and to make "polytope" vectors, i.e., constructs which encode a plurality of useful peptides.

The foregoing examples describe the isolation and characterization of a peptide from NY-ESO-1 which binds promiscuously to MHC Class II molecules, particularly HLA-DR and serves as a T cell epitope for $CD4^+$ cells when bound to the Class II molecules.

Also a part of the invention are expression vectors which incorporate the nucleic acid molecules described herein in operable linkage (i.e., "operably linked") to a promoter. Construction of such vectors is well within the skill of the art, as is the transformation or transfection of cells, to produce eukaryotic cell lines, or prokaryotic cell strains which encode the molecule of interest. Exemplary of the host cells which can be employed in this fashion are COS cells, CHO cells, yeast cells, insect cells (e.g., *Spodoptera frugiperda*), NIH 3T3 cells, and so forth. Prokaryotic cells, such as *E. coli* and other bacteria may also be used.

As is clear from the disclosure, one may use the peptides and nucleic acid molecules of the invention diagnostically. The SEREX methodology discussed herein is premised on an immune response to a pathology associated antigen. Hence, one may assay for the relevant pathology via, e.g., testing a body fluid sample of a subject, such as serum, for reactivity with the antigen per se. Reactivity would be deemed indicative of possible presence of the pathology. One could assay for antibodies against the subject molecule, using standard immuno assays as well.

Similarly, the invention contemplates therapies wherein the nucleic acid molecule which encodes one or more peptides, including the NY-ESO-1 derived peptide of the invention is incorporated into a vector, such as an adenovirus based vector, to render it transfectable into eukaryotic cells, such as human cells. Similarly, nucleic acid molecules which encode one or more of the peptides may be incorporated into these vectors, which are then the major constituent of nucleic acid bases therapies.

Any of these assays can also be used in progression/regression studies. One can monitor the course of abnormality involving expression of NY-ESO-1, simply by monitoring levels of $CD4^+$ specific to the peptide using any or all of the methods set forth supra, including ELISPOT, and tetrameric assays.

It should be clear that these methodologies may also be used to track the efficacy of a therapeutic regime. Essentially, one can take a baseline value for the $CD4^+$ cells using any of the assays discussed supra, administer a given therapeutic agent, and then monitor levels of the $CD4^+$ thereafter, observing changes therein as indicia of the efficacy of the regime.

As was indicated supra, the invention involves, inter alia, the recognition of an "integrated" immune response to the NY-ESO-1 molecule. One ramification of this is the ability to monitor the course of cancer therapy. In this method, which is a part of the invention, a subject in need of the therapy receives a vaccination of a type described herein. Such a vaccination results, e.g., in a coordinate $CD4^+/CD8^+$ T and B cell response against cells presenting HLA/peptide complexes on their cells and corresponding B cell responses. Hence, one can monitor the effect of a vaccine, by monitoring an immune response. As is indicated, supra, an increase in antibody titer and/or T cell count following antigen specific vaccination may be taken as an indicia of progress with a vaccine, and vice versa. Hence, a further aspect of the invention is a method for monitoring efficacy of a vaccine, following administration thereof, by determining levels of antibodies, $CD4^+$, and/or $CD8^+$ levels in the subject which are specific for the vaccine itself; or a large molecule of which the vaccine is apart.

The effects of a vaccine can also be measured by monitoring the CD4⁺ cell response of the subject receiving the vaccine. A number of assays can be use to measure the precursor frequency of these in vitro stimulated T cells. These include, but are not limited to, chromium release assays, TNF release assays, IFN-γ release assays, an ELISPOT assay, and so forth. Changes in precursor T cell frequencies can be measured and correlated to the efficacy of the vaccine. Additional methods which can be employed include the use of multimeric complexes of MHC/peptides. An example of such complexes is the tetrameric HLA/peptide-biotin-streptavidin system of Dunbar, et al., Curr. Biol. 8:413-416 (1998), incorporated by reference.

Also a part of this invention are antibodies, e.g., polyclonal and monclonal, and antibody fragments, e.g., single chain Fv, Fab, diabodies, etc., that specifically bind the peptides or HLA/peptide complexes disclosed herein. Preferably, the antibodies, the antibody fragments and T cell receptors bind the HLA/peptide complexes in a peptide-specific manner. Such antibodies are useful, for example, in identifying cells presenting the HLA/peptide complexes. Such antibodies are also useful in promoting the regression or inhibiting the progression of a tumor which expresses complexes of the HLA and peptide. Polyclonal antisera and monoclonal antibodies specific to the peptides or HLA/peptide complexes of this invention may be generated according to standard procedures. See e.g., Catty, D., Antibodies, A Practical Approach, Vol. 1, IRL Press, Washington D.C. (1988); Klein, J. Immunology: The Science of Cell-Non-Cell Discrimination, John Wiley and Sons, New York (1982); Kennett, R., et al., Monoclonal Antibodies, Hybridoma, A New Dimension In Biological Analyses, Plenum Press, New York (1980); Campbell, A., Monoclonal Antibody Technology, in Laboratory Techniques and Biochemistry and Molecular Biology, Vol. 13 (Burdon, R. et al. EDS.), Elsevier Amsterdam (1984); Eisen, H. N., Microbiology, third edition, Davis, B. D. et al. EDS. (Harper & Rowe, Philadelphia (1980); Kohler and Milstein, Nature, 256:495 (1975) all incorporated herein by reference.) Methods for identifying Fab molecules endowed with the antigen-specific, HLA-restricted specificity of T cells has been described by Denkberg et al. PNAS 99:9421-9426 (2002) and Cohen et al. Cancer Research 62:5835-5844 (2002) both incorporated herein by reference). Methods for generating and identifying other antibody molecules, e.g., scFv and diabodies are well known in the art, see e.g., Bird et al., Science, 242:423-426 (1988); Huston et al., Proc. Natl. Acad. Sci., 85:5879-5883 (1988); Mallender and Voss, J. Biol. Chem. 269:199-206 (1994); Ito and Kurosawa, J Biol Chem 27: 20668-20675 (1993), and; Gandecha et al., Prot Express Purif. 5: 385-390 (1994).

The antibodies of this invention can be used for experimental purposes (e.g. localization of the HLA/peptide complexes, immunoprecipitations, Western Blots, flow cytometry, ELISA etc.) as well as diagnostic or therapeutic purposes, e.g., assaying extracts of tissue biopsies for the presence of HLA/peptide complexes, targeting delivery of cytotoxic or cytostatic substances to cells expressing the appropriate HLA/peptide complex. The antibodies of this invention are useful for the study and analysis of antigen presentation on tumor cells and can be used to assay for changes in the HLA/peptide complex expression before, during or after a treatment protocol, e.g., vaccination with peptides, antigen presenting cells, HLA/peptide tetramers, adoptive transfer or chemotherapy. The antibodies and antibody fragments of this invention may be coupled to diagnostic labeling agents for imaging of cells and tissues that express the HLA/peptide complexes or may be coupled to therapeutically useful agents by using standard methods well-known in the art. The antibodies also may be coupled to labeling agents for imaging e.g., radiolabels or fluorescent labels, or may be coupled to, e.g., biotin or antitumor agents, e.g., radioiodinated compounds, toxins such as ricin, methotrexate, cytostatic or cytolytic drugs, etc. Examples of diagnostic agents suitable for conjugating to the antibodies of this invention include e.g., barium sulfate, diatrizoate sodium, diatrizoate meglumine, iocetamic acid, iopanoic acid, ipodate calcium, metrizamide, tyropanoate sodium and radiodiagnostics including positron emitters such as fluorine-18 and carbon-11, gamma emitters such as iodine-125, technitium-99m, iodine-131 and indium-111, nuclides for nuclear magnetic resonance such as fluorine and gadolinium. As used herein, "therapeutically useful agents" include any therapeutic molecule which are preferably targeted selectively to a cell expressing the HLA/peptide complexes, including antineoplastic agents, radioiodinated compounds, toxins, other cytostatic or cytolytic drugs. Antineoplastic therapeutics are well known and include: aminoglutethimide, azathioprine, bleomycin sulfate, busulfan, carnustine, chlorambucil, cisplatin, cyclophosphamide, cyclosporine, cytarabidine, dacarbazine, dactinomycin, daunorubicin, doxorubicin, taxol, etoposide, fluorouracil, interferon-.alpha., lomustine, mercaptopurine, methotrexate, mitotane, procarbazinle HCl, thioguamine, vinblastine sulfate and vincristine sulfate. Additional antinieoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division). Toxins can be proteins such as, for example, pokeweed anti-viral protein, cholera toxin, peltussis toxin, ricin, gelonin, abrin, diphtheria exotoxin, or Pseudomonas exotoxin. Toxin moieties can also be high energy-emitting radionuclides such as cobalt-60. The antibodies may be administered to a subject having a pathological condition characterized by the presentation of the HLA/peptide complexes of this invention, e.g., melanoma and several other cancers, as described in Jungbluth et al., Int. J. Cancer, 92:856-860 (Jun. 15, 2001, incorporated herein by reference), in an amount sufficient to alleviate the symptoms associated with the pathological condition.

Soluble T cell receptors (sTCRs) which specifically bind to the HLA/peptide complexes described herein are also an aspect of this invention. In their soluble form T cell receptors are analogous to a monoclonal antibody in that they bind to HLA/peptide complex in a peptide-specific manner. Immobilized TCRs or antibodies may be used to identify and purify unknown peptide/HLA complexes which may be involved in cellular abnormalities. Methods for identifying and isolating sTCRs are known in the art, see for example WO 99/60119, WO 99/60120 (both incorporated herein by reference) which describe synthetic multivalent T cell receptor complex for binding to peptide-MHC complexes. Recombinant, refolded soluble T cell receptors are specifically described. Such receptors may be used for delivering therapeutic agents or detecting specific peptide-MHC complexes expressed by tumor cells. WO 02/088740 (incorporated by reference) describes a method for identifying a substance that binds to a peptide-MHC complex. A peptide-MHC complex is formed between a predetermined MHC and peptide known to bind to such predetermined MHC. The complex is then use to screen or select an entity that binds to the peptide-MHC complex such as a T cell receptor. The method could also be applied to the selection of monoclonal antibodies that bind to the predetermined peptide-MHC complex.

Also an embodiment of this invention are nucleic acid molecules encoding the antibodies and T cell receptors of this invention and host cells, e.g., human T cells, transformed with a nucleic acid molecule encoding a recombinant antibody or antibody fragment, e.g., scFv or Fab, or a TCR specific for a pre-designated HLA/peptide complex as described herein. Recombinant Fab or TCR specific for a pre-designated HLA/peptide complex in T cells have been described in, e.g., Willemsen et al., "A phage display selected fab fragment with MHC class I-restricted specificity for MAGE-A1 allows for retargeting of primary human T lymphocytes" Gene Ther. 2001 November; 8(21):1601-8. PMID: 11894998 [PubMed—indexed for MEDLINE] and Willemsen et al., "Grafting primary human T lymphocytes with cancer-specific chimeric single chain and two chain TCR". Gene Ther. 2000 August; 7(16):1369-77. PMID: 10981663 [PubMed—indexed for MEDLINE] (both incorporated herein by reference) and have applications in an autologous T cell transfer setting. The autologous T cells, transduced to express recombinant antibody or sTCR, may be infused into a patient having an pathological condition associated with cells expressing the HLA/peptide complex. The transduced T cells are administered in an amount sufficient to inhibit the progression or alleviate at least some of the symptoms associated with the pathological condition.

An embodiment of this invention is a method for promoting regression or inhibiting progression of a tumor in a subject in need thereof wherein the tumor expresses a complex of HLA and peptide. The method comprises administering an antibody, antibody fragment or soluble T cell receptor, which specifically binds to the HLA/peptide complex, or by administering cells transduced so that they express those antibodies or TcR in amounts that are sufficient to promote the regression or inhibit progression of the tumor expressing the HLA/peptide complex, e.g., a melanoma or other cancer. The antibodies, antibody fragments and soluble T cell receptors may be conjugated with, or administered in conjunction with, an antineoplastic agent, e.g., radioiodinated compounds, toxins such as ricin, methotrexate, or a cytostatic or cytolytic agent as discussed supra. See e.g., Patan et al., Biochem. Biophys. Acta, 133:C1-C6 (1997), Lode et al., Innunol. Res. 21:279-288 (2000) and Wihoff et al. Curr. Opin. Mo. Ther. 3:53-62 (2001) (all incorporated herein by reference) for a discussion of the construction of recombinant immunotoxins, antibody fusions with cytokine molecules and bispecific antibody therapy or immunogene therapy.

Other features and applications of the invention will be clear to the skilled artisan, and need not be set forth herein.

The terms and expression which have been employed are used as terms of description and not of limitation, and there is no intention in the use of such terms and expression of excluding any equivalents of the features shown and described or portions thereof, it being recognized that various modifications are possible with the scope of the invention.

What is claimed is:

1. A composition useful in stimulating a T cell response comprising an isolated peptide consisting of the amino acid sequence set forth in SEQ ID NO: 2, wherein said peptide binds to an MHC-Class II molecule selected from the group consisting of HLA-DRβ1*0101, HLA-DRβ1*0301, HLA-DRβ1*0401, and HLA-DRβ1*0701 and is stimulatory for T cells restricted to complexes of SEQ ID NO: 2 and any one of said MHC Class II molecules, and an adjuvant.

2. A composition useful in stimulating a T cell response in a subject, comprising the composition of claim 1, and at least one additional peptide.

3. The composition of claim 2, wherein said at least one additional peptide consists of an amino acid sequence found in NY-ESO-1.

4. The composition of claim 2, wherein said at least one additional peptide binds to an MHC Class I molecule and stimulates a CD8+ T cell response.

5. The composition of claim 2, wherein said at least one additional peptide binds to an MHC Class II molecule and stimulates a CD4+ T cell response.

6. The composition of claim 2, further comprising a pharmaceutically acceptable carrier.

7. The composition of claim 6, wherein said pharmaceutically acceptable carrier is an adjuvant.

* * * * *

SEQUENCE LISTING

```
<160> NUMBER OF SEQ ID NOS: 5

<210> SEQ ID NO 1
<211> LENGTH: 15
<212> TYPE: PRT
<213> ORGANISM: H. Sapiens
<220> FEATURE:

<400> SEQUENCE: 1

Tyr Leu Ala Met Pro Phe Ala Thr Pro Met Glu Ala Glu Leu Ala
                5                   10                  15

<210> SEQ ID NO 2
<211> LENGTH: 15
<212> TYPE: PRT
<213> ORGANISM: H. Sapiens
<220> FEATURE:

<400> SEQUENCE: 2

Thr Ile Arg Leu Thr Ala Ala Asp His Arg Gln Leu Gln Leu Ser
                5                   10                  15

<210> SEQ ID NO 3
<211> LENGTH: 15
<212> TYPE: PRT
<213> ORGANISM: H. Sapiens
<220> FEATURE:

<400> SEQUENCE: 3

Leu Leu Met Trp Ile Thr Gln Cys Phe Leu Pro Val Phe Leu Ala
                5                   10                  15

<210> SEQ ID NO 4
<211> LENGTH: 15
<212> TYPE: PRT
<213> ORGANISM: H. Sapiens
```

```
<220> FEATURE:

<400> SEQUENCE: 4

Phe Ile Arg Leu Thr Ala Ala Asp His Arg Gln Leu Gln Leu Ser
                5                   10                  15

<210> SEQ ID NO 5
<211> LENGTH: 15
<212> TYPE: PRT
<213> ORGANISM: H. Sapiens
<220> FEATURE:

<400> SEQUENCE: 5

His Ile Thr Met Pro Phe Ser Ser Pro Met Glu Ala Glu Leu Val
                5                   10                  15
```